United States Patent [19]

Bloom

[11] Patent Number: 4,458,778
[45] Date of Patent: Jul. 10, 1984

[54] STETHOSCOPE CONSTRUCTION

[76] Inventor: Max Bloom, 335 Hope St., Providence, R.I. 02906

[21] Appl. No.: 246,579

[22] Filed: Mar. 23, 1981

[51] Int. Cl.³ .............................................. A61B 7/02
[52] U.S. Cl. .................................... 181/131; 181/137; 181/158
[58] Field of Search ............... 181/131, 137, 158, 129; 179/1 SK

[56] References Cited

U.S. PATENT DOCUMENTS 3,067,833  12/1962  Bodenger ........................... 181/137
3,224,526  12/1965  Weber ................................. 181/137
3,543,875  12/1970  Littmann ............................ 181/137

Primary Examiner—Benjamin R. Fuller
Attorney, Agent, or Firm—Salter & Michaelson

[57] ABSTRACT

A microphone for stethoscopes and the like having a weighted head member with a recessed cavity formed therein. A diaphragm is sealed to the head member with an adhesive material to provide an airtight cover for the cavity. The mass of the head member causes it to remain substantially vibration free and as a result all vibrations are transmitted directly to the diaphragm causing it to vibrate with increased amplitude at all frequencies. The adhesive seal between the diaphragm and the head member effectively eliminates secondary vibration thereof so that the microphone is capable of producing a distortion free air signal of high amplitude at all normal frequencies.

1 Claim, 5 Drawing Figures

U.S. Patent  Jul. 10, 1984  4,458,778
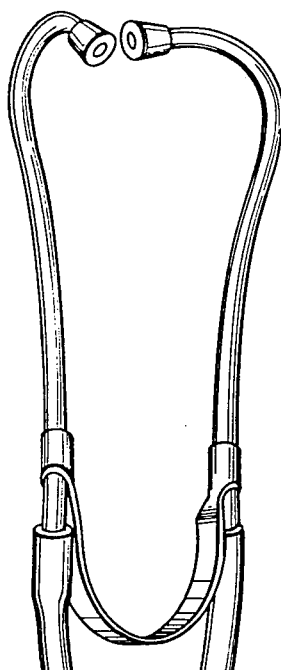
FIG. 1
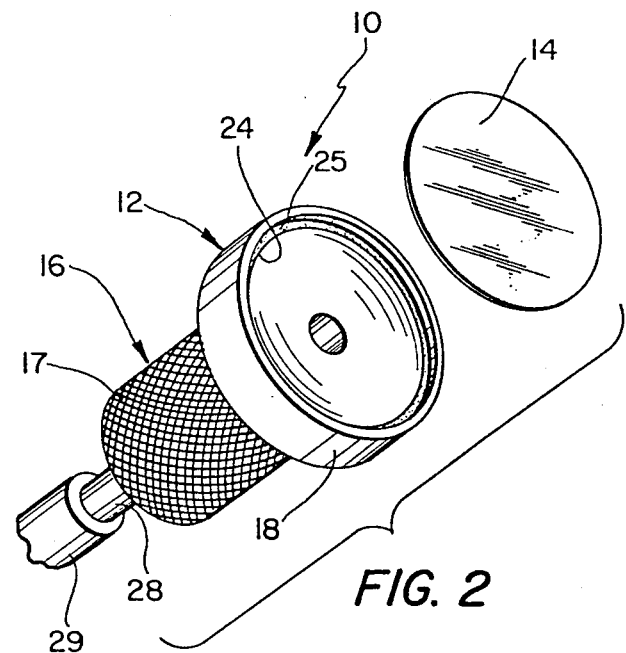
FIG. 2
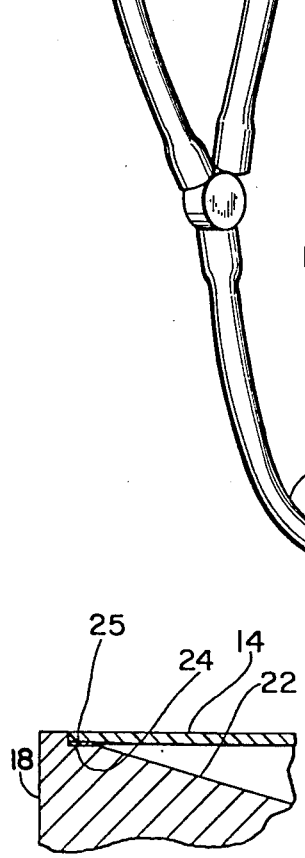
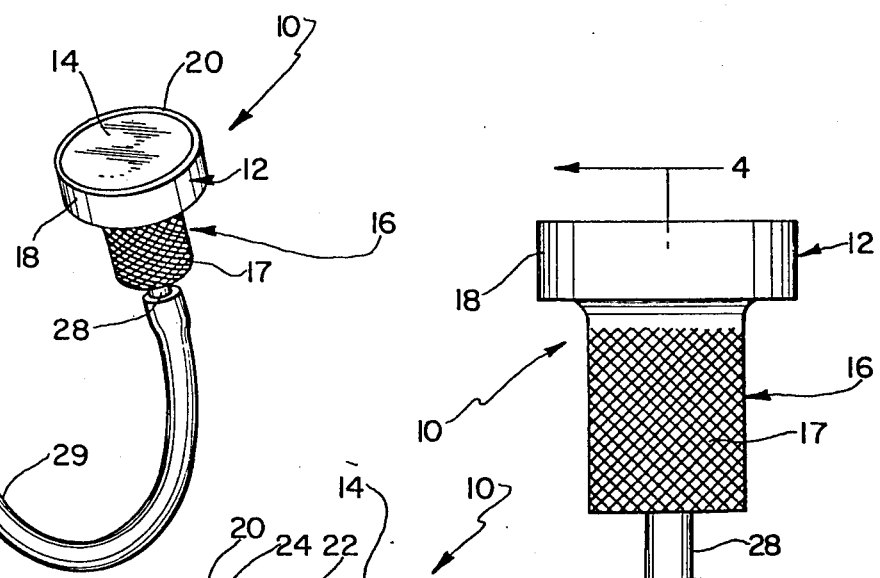
FIG. 3
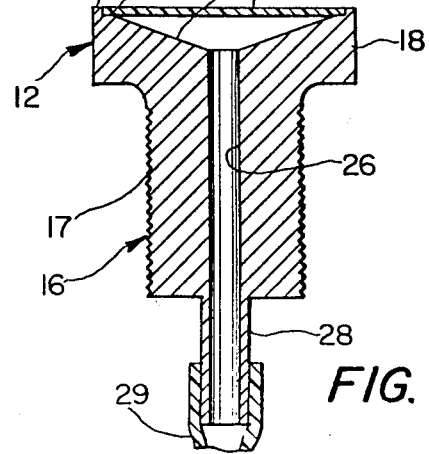
FIG. 5
FIG. 4

STETHOSCOPE CONSTRUCTION

BACKGROUND OF THE INVENTION

The instant invention relates to stethoscopes and the like and more particularly to a novel construction for the microphone portion thereof.

Stethoscopes have for years been one of the primary instruments relied upon by physicians in diagnosing and detecting certain types of ailments in patients. The microphone portion of a stethoscope is positioned in engagement with a portion of a patient's body and the physician is able to listen to the sounds emanating therefrom, to enable him to make his diagnosis.

Traditional stethoscope microphone constructions have included a head member with a diaphragm attached thereto which vibrates in response to sound waves when positioned in engagement with a patient's body. As the diaphragm vibrates it causes compression in a cavity in the microphone and the compression is transmitted through tubular members to ear pieces which are positionable in the physician's ears. Previously known diaphragm type microphones have not been completely effective throughout the entire frequency range of sounds normally associated with the human body and consequently combination stethoscope microphones have been available which have combined a bell type microphone with the conventional diaphragm type microphone to extend the range of the microphone to cover very low frequency vibrations. An example of this type of device is shown in the U.S. Patent to LITTMAN, No. 3,108,652.

While it is certainly important to provide a microphone which will detect sounds and vibrations in all of the frequency ranges normally characteristic of sounds emanating from the human body, it is also important to provide a microphone which produces a clear, audible signal. One of the main deficiencies of previously known diaphragm type microphones has been their inability to produce a clear signal as a result of secondary vibrations created between the diaphragm and the head portion of the microphone. In conventional microphone constructions the diaphragm has been secured to the head portion by crimping or pinching a portion of the head, but no matter how effectively this is done, independent secondary vibrations tend to develop in the diaphragm. As a result, the signal which is produced is not always distortion free and may not always give the physician a clear indication of the patient's condition.

The instant invention overcomes these and other drawbacks by providing a stethoscope microphone having a diaphragm which is capable of faithfully following the heartbeat or other vibration in the patient's body to provide a clear accurate transmission thereof at a level which is easily audible. Consequently the microphone can detect sounds and vibrations throughout the entire frequency range of sounds normally associated with the human body thereby providing a substantial improvement in the art of stethoscope microphones.

SUMMARY OF THE INVENTION

The instant invention relates to stethoscopes and the like and more particularly to a novel construction for the microphone portion thereof.

The stethoscope microphone of the instant invention includes a weighted head member having a recessed cavity therein. A diaphragm is provided covering the cavity and is secured to the head member with an airtight adhesive seal around its periphery. As a result of the weighted characteristic of the head member, substantially all of the detectable sounds in a patient's body are transmitted directly to the diaphragm and the head member remains substantially vibration free. Since all of the vibrations are transmitted directly to the diaphragm, the microphone of the instant invention is able to produce a sound signal of considerably greater amplitude than could microphones heretofore available. Consequently, the microphone of the instant invention is effective for detecting vibrations throughout the entire frequency range of vibrations normally associated with the human body and the necessity for adding a bell or other device to extend the range of the microphone is eliminated. Furthermore, since the diaphragm is sealed to the head member in an airtight manner with an adhesive material, secondary vibrations between the diaphragm and the head member are virtually eliminated and a clear distortion-free signal is produced by the microphone.

It is therefore an object of the instant invention to provide a microphone for stethoscopes and the like which is capable of detecting vibrations throughout the entire frequency range of vibrations normally associated with the human body.

Another object of the instant invention is to provide a microphone for a stethoscope which uses a weighted head member so that virtually all of the vibrations detected by the microphone are transmitted directly to the diaphragm portion thereof.

A further object of the instant invention is to provide a microphone for stethoscopes and the like which is capable of producing a distortion-free signal.

A still further object of the instant invention, is to provide a microphone for stethoscopes and the like which has a diaphragm which is virtually free from secondary vibrations.

Other objects, features and advantages of the invention shall become apparent as the description thereof proceeds when considered in connection with the accompanying illustrative drawing.

DESCRIPTION OF THE DRAWING

In the drawing which illustrates the best mode presently contemplated for carrying out the present invention:

FIG. 1 is a perspective view of a stethoscope including the microphone of the instant invention;

FIG. 2 is an exploded perspective view of the stethoscope microphone of the instant invention;

FIG. 3 is a side elevational view thereof;

FIG. 4 is side sectional view thereof taken along line 4—4 in FIG. 3; and

FIG. 5 is an enlarged fragmentary side sectional view of a portion of the microphone particularly illustrating the attachment of the diaphragm to the head member thereof.

DESCRIPTION OF THE INVENTION

Referring now to the drawing, the stethoscope microphone of the instant invention is shown in FIGS. 1 through 4 and is generally indicated at 10. As will be noted, particularly from FIG. 2, the stethoscope microphone 10 comprises a weighted head member generally indicated at 12 with a diaphragm 14 attached thereto.

Although various suitable construction materials are available for the head member 12, preferably it is constructed of a corrosion resistant metal such as stainless steel. The preferred configuration of the head member 12 is particularly illustrated in FIGS. 2, 3 and 4 and as will be noted, is generally circular having a cylindrical neck portion 16 which may be knurled as at 17 to facilitate the gripping thereof and an enlarged facing portion 18. A substantially circular rim 20 extends around the periphery of the end of the facing portion 18 and a concave recessed cavity 22 of substantially circular cross section having a marginal shoulder portion 24 is provided. A passage 26 extends from substantially the center of the recessed cavity 22 axially through the head member 12 to a tubular extension 28 whereby an air signal may be transmitted to the listening or transmission portion of the stethoscope. As illustrated in FIG. 1, the microphone 10 is attachable to the flexible conduit 29 of the transmission portion of a stethoscope generally indicated at 30 for transmission of the sound waves to the ears of a physician. The transmission portion 30 is of conventional construction and may be of the general type illustrated in the aforesaid LITTMAN patent.

The diaphragm 14 may be made of any suitable plastic, metal or other material and preferably has a thickness of between 0.010 and 0.030 inches. The diaphragm 14 is of substantially circular configuration being dimensioned to fit snugly within the rim 20, resting on the shoulder 24. In order to prevent secondary vibrations between the diaphragm 14 and the head member 12, the diaphragm is secured thereto in an airtight manner with an adhesive material 25 around its periphery.

As hereinbefore stated, the head portion 12 is constructed of a weighted material such as stainless steel. Consequently when the diaphragm 14 is positioned in engagement with a portion of a patient's body, substantially all of the detectable vibrations are transmitted directly to the diaphragm 14 and the head member 12 as a result of its substantial mass, remains substantially motionless and vibration-free. Furthermore, since substantially all of the vibrations are transmitted directly to the diaphragm, the diaphragm vibrates to produce a signal which is of sufficient amplitude to be detectable throughout the entire range of frequencies of vibrations normally associated with the human body. While there is a direct relationship between the size and weight of the head member and the relative tendency thereof to remain vibration free, practical considerations obviously limit the size and weight of the microphone 10. It has been determined through experimentation that the optimum weight of the head member 12 is approximately 10 ounces. It has been found that microphones with head members of approximately this weight are capable of producing high amplitude signals but nevertheless are still practical for every day use by a physician.

As hereinbefore noted, the diaphragm 14 is sealed to the head member 12 with an adhesive material 25 to provide an airtight seal therebetween. Traditionally, diaphragms have been attached to the head members of microphones by crimping or pinching a portion of the head member over the marginal edge of the diaphragm. With this type of attachment it is virtually impossible to eliminate all relative movement between the diaphragm and the head, thus resulting in secondary vibrations between the diaphragm and the head member which tend to distort the primary vibration and therefore reduce the clarity of the signal which is produced.

Also, since an attachment of this type is not airtight, compression within the cavity caused by the vibrating diaphragm is somewhat reduced, thus decreasing the amplitude of the signal being produced. By providing an adhesive seal between the diaphragm and the head member, secondary vibrations are eliminated; and as a result, the microphone of the instant invention provides a much clearer, more accurate signal for transmission than previously known microphones. Furthermore, the airtight characteristics of the microphone herein described, in addition to effecting maximum amplitude of the sound signal, also are desirable from a hygenic standpoint, since the entry of dirt or other foreign particles to the cavity 22 is prevented.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A microphone for stethoscopes and the like comprising:
   a. a metallic head member having a recessed cavity formed therein with an interior passage extending from said cavity to the exterior of said head member, said head member having a weight of at least approximately 10 ounces;
   b. a diaphragm attached to said head member covering said cavity in an airtight manner;
   c. connecting means for securing said head member to the transmission portion of a stethoscope and the like and providing an airtight relationship between said transmission portion and said passage.

* * * * *